United States Patent [19]

Gutcheck et al.

[11] Patent Number: 5,258,616
[45] Date of Patent: Nov. 2, 1993

[54] OPTICAL DISTRIBUTION SYSTEM INCORPORATING AN IMPROVED ABSORBANCE-BASED OPTICAL FIBER SENSOR

[75] Inventors: Robert A. Gutcheck, Bothell; Maxie W. Fields, Jr., Des Moines; Tim C. Reynolds, Mill Creek; Scott M. Dennison, Seattle, all of Wash.

[73] Assignee: Abbott Laboratories, Abbott Park, Ill.

[21] Appl. No.: 961,740

[22] Filed: Oct. 15, 1992

[51] Int. Cl.⁵ .............................................. H01J 5/16
[52] U.S. Cl. .......................... 250/227.21; 250/227.23
[58] Field of Search ...................... 250/227.17, 227.21, 250/227.23; 385/12; 422/82.05, 82.06

[56] References Cited

U.S. PATENT DOCUMENTS 5,059,790  10/1991  Klainer et al. ................. 250/227.21
5,094,958   3/1992  Klainer et al. ................. 250/227.23

*Primary Examiner*—David C. Nelms
*Assistant Examiner*—K. Shami
*Attorney, Agent, or Firm*—Harry G. Thibault; Robert E. Wexler

[57] ABSTRACT

An optical distribution system incorporating improved absorbance-based optical fiber sensor incorporating fiber optic couplers, thereby eliminating fiber optic connectors in the system to provide improved efficiency and improved output in the system, the system further incorporating specific thermal stabilizing mechanisms to improve the stability of the system and a specific construction for the photodiode assembly to minimize internal reflection therein.

8 Claims, 5 Drawing Sheets

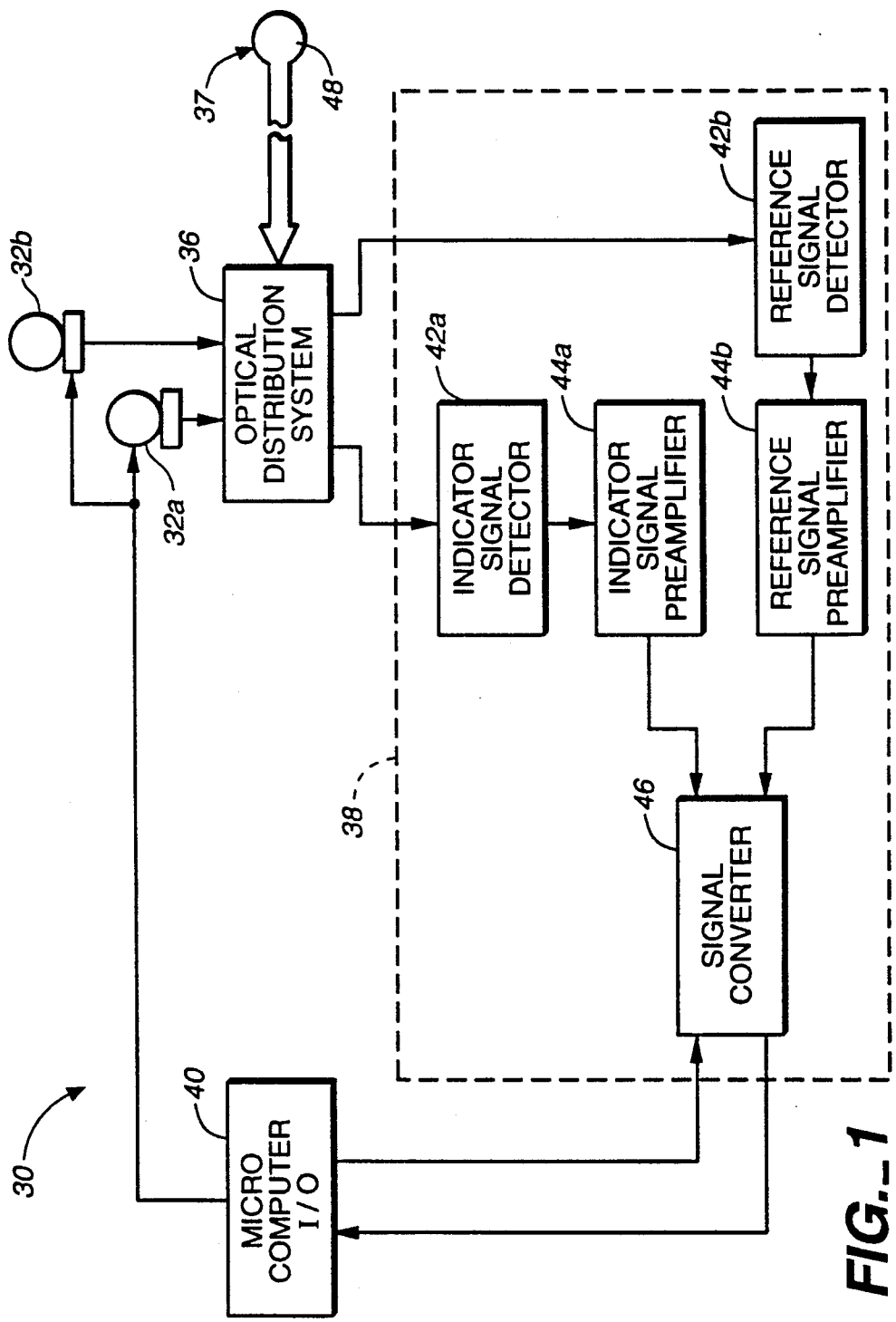
FIG._1

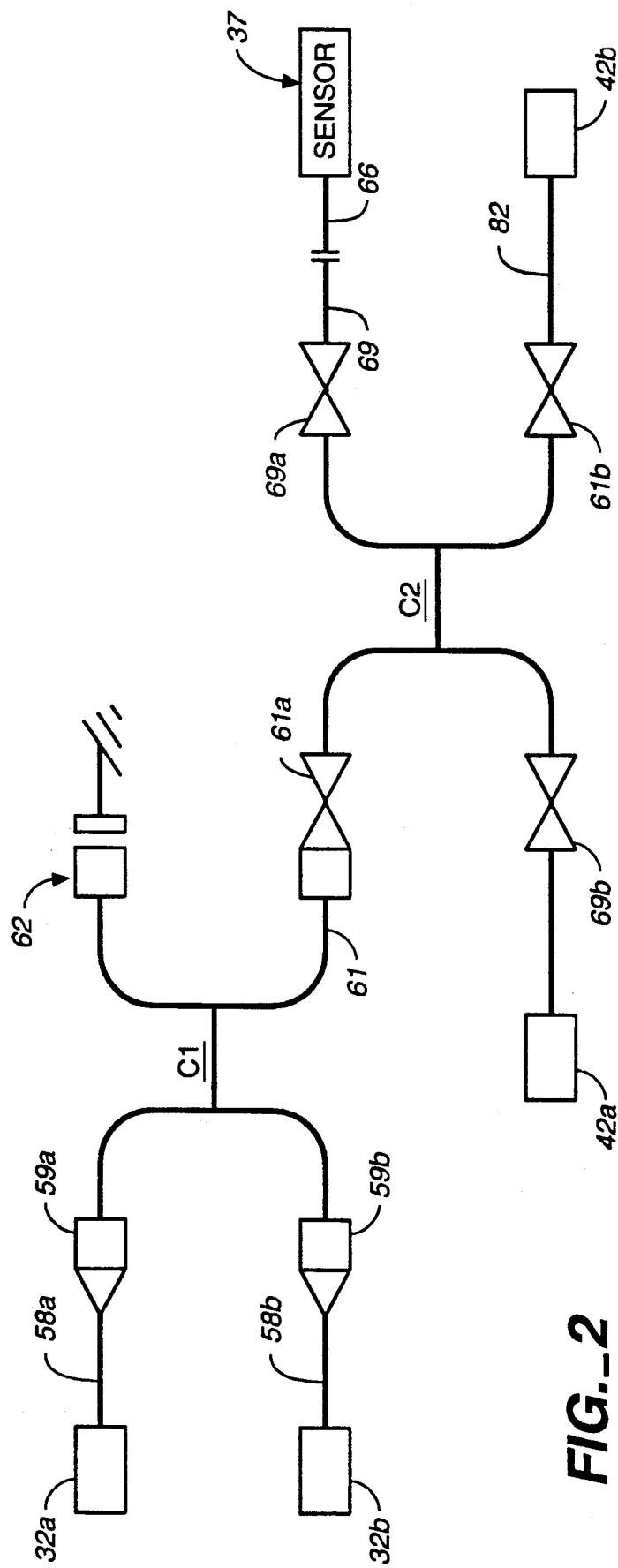
FIG._2

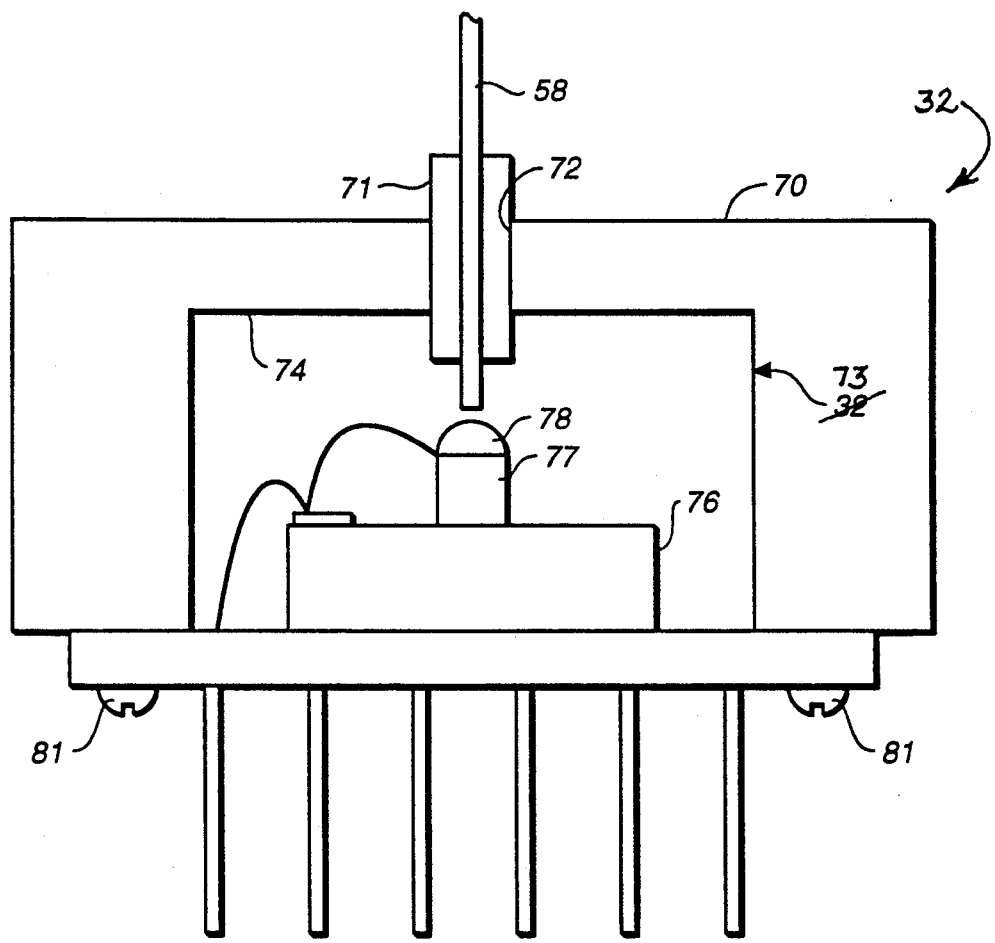
FIG._3
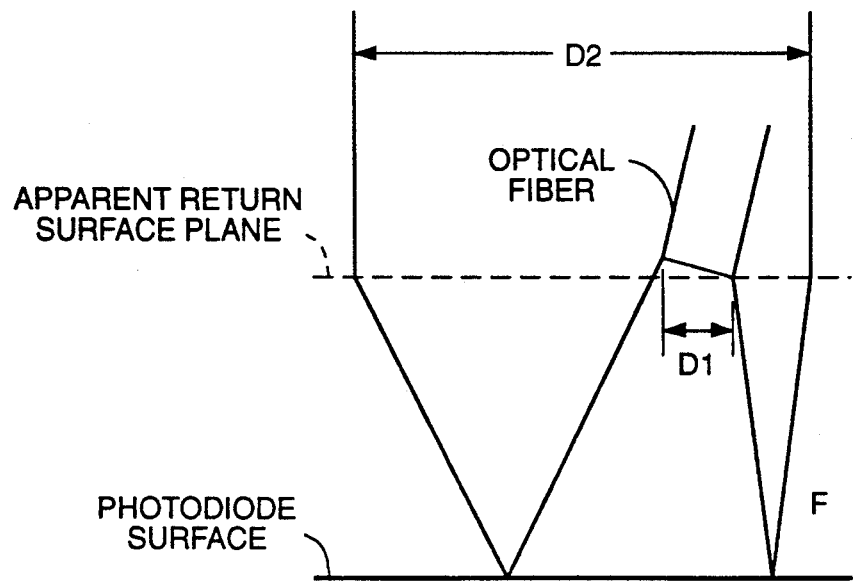
FIG._6

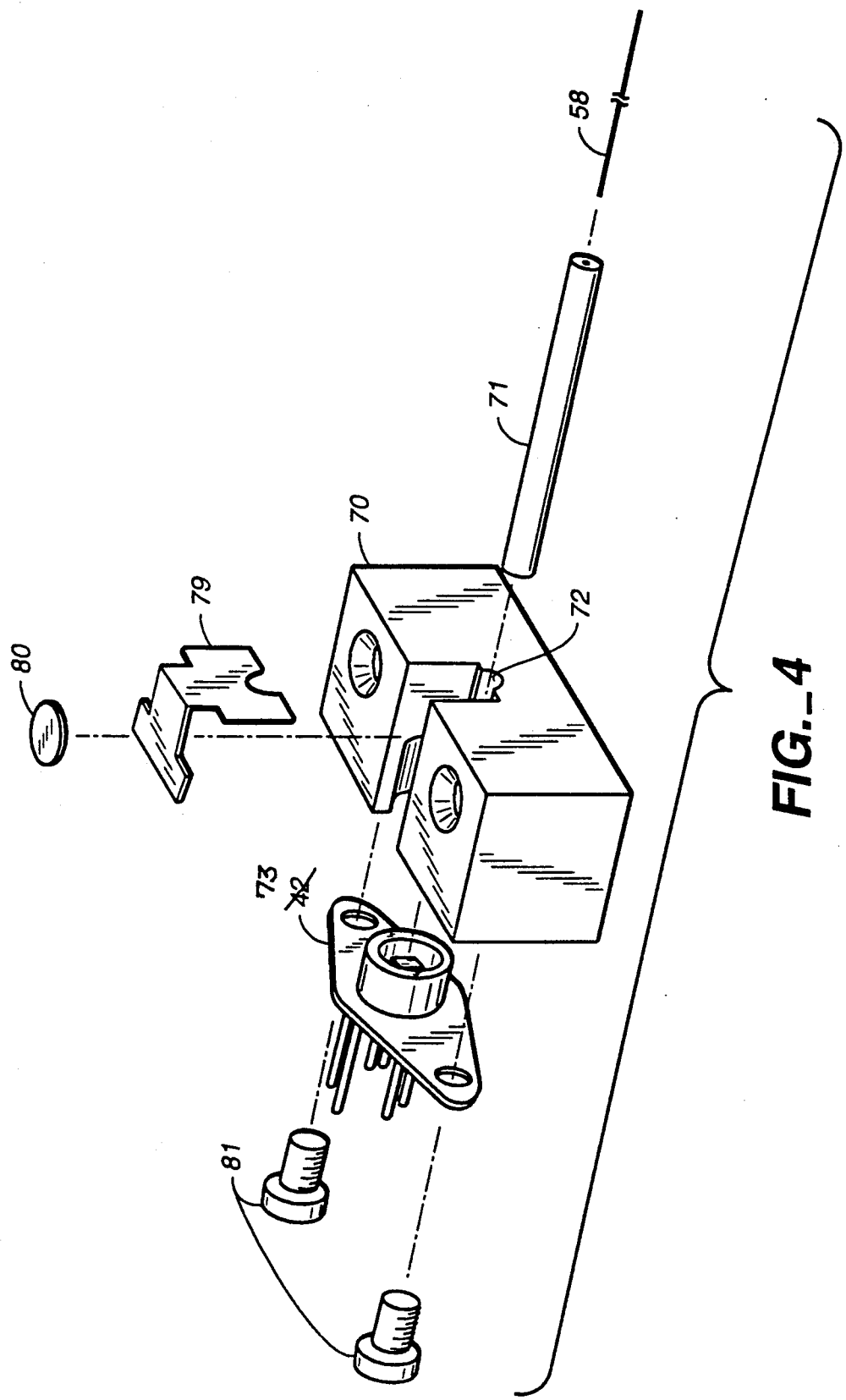
FIG._4

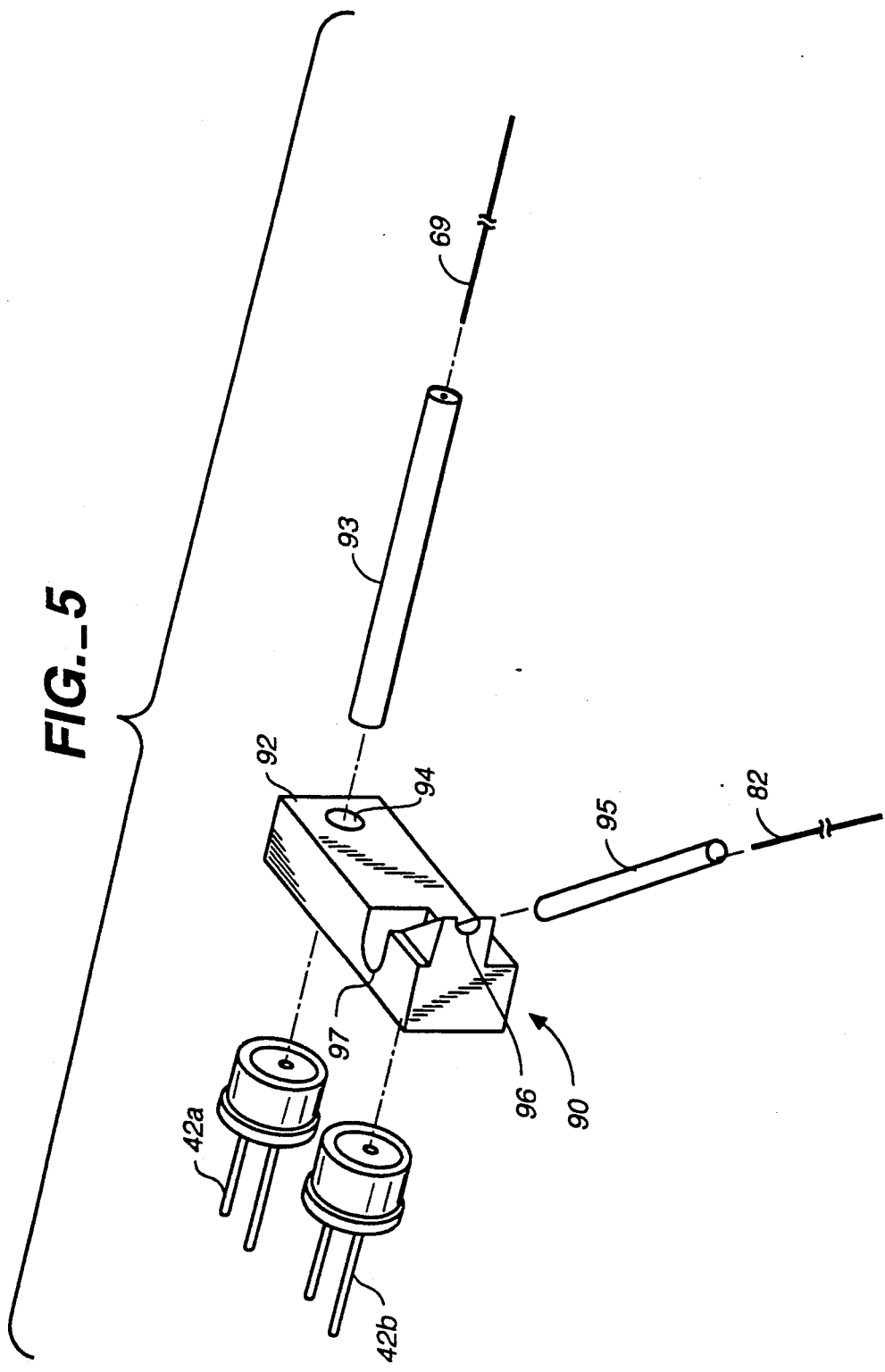

OPTICAL DISTRIBUTION SYSTEM INCORPORATING AN IMPROVED ABSORBANCE-BASED OPTICAL FIBER SENSOR

This invention relates to an optical distribution system suitable for use in an optical fiber sensor system and, more particularly, for use in an optical fiber sensor system having a sensor tip made up of a single fiber and incorporating optical wavelength sensitive indicators to monitor analyte concentrations in compositions, and having distribution system monitoring capabilities.

RELATED APPLICATIONS

An optical signal distribution system incorporating an improved luminescent sensor is described in co-pending U.S. application Ser. No. 07/961,559 filed Oct. 15, 1992 and assigned to the assignee of the subject application.

BACKGROUND OF THE INVENTION

Optical fiber sensors have been developed to detect the presence and monitor the concentration of various analytes, including oxygen, carbon dioxide, glucose, inorganic ions, and hydrogen ions, in liquids and in gases. Such sensors are based on the recognized phenomenon that the absorbance or luminescence of certain indicator molecules is specifically perturbed in the presence of certain analytes. The perturbation in the absorbance and/or luminescence profile can be detected by monitoring radiation that is reflected, absorbed, transmitted, or emitted by the indicator molecule when it is in the presence of a specific analyte. The targeted analyte is generally a part of a solution containing a variety of analytes.

Duofiber optical sensors have been developed that position an analyte-sensitive indicator molecule in the light path of a sensor tip. The indicator molecule is typically housed in a sealed chamber whose walls are permeable to the analyte. The sealed chamber is submerged in the analyte-containing solution. The sensor tip includes a pair of optical fibers. The term "duofiber" refers to the number of fibers in the sensor tip. In comparison, a "single-fiber" sensor utilizes only one fiber in the sensor tip. In a duofiber sensor, one fiber transmits electromagnetic radiation, termed measuring signal, from a signal-generating component to the indicator molecule. The other fiber transmits the reflected or emitted light, termed indicator signal, from the sensor tip to a signal-measuring component that measures the indicator signal intensity. The configuration of the optical fibers between the signal-generating component, the sensor tip, and the signal-measuring component describes the optical fiber distribution system for the sensor system.

Although there are two common types of sensor systems, absorption and luminescent, the present invention is used in conjunction with an absorption system. In an absorption system, an analyte-sensitive dye is typically housed in the sealed chamber of the sensor tip. The system operates on the concept of optically detecting the change in color of the analyte-sensitive dye. This is done by measuring the intensity of the measuring signal reflected or unabsorbed at the sensor tip and comparing it to the intensity of the original measuring signal to determine the portion of the measuring signal that was absorbed by the dye at the sensor tip. Suitable analyte-sensitive indicator molecules are known in the art and are selected based upon the particular analyte substance whose detection is targeted.

The optical fiber distribution system is an integral part of each optical fiber sensor system. Typical distribution systems are made up of optical fibers and optical connectors. The distribution system directs the measuring signal from the signal-generating component to the sensor tip and also directs the reflected or emitted indicator signal from the sensor tip to the signal-measuring component. In a sensor using an absorption monitoring technique, the distribution system will additionally direct a portion of the measuring signal directly to the signal-measuring component. A determination of the quantity of a specific analyte is then made by comparing the intensity of the measuring signal to the intensity of the indicator signal.

The efficiency and reliability of a sensor system largely depends on its optical fiber distribution system. Although current optical fiber technology may not provide a one hundred percent signal transfer at fiber connection points, the signal reduction at optical fiber connections should be ascertainable and controllable. Variability in analyte concentration measurements that may be related to the optical fiber distribution system arise from fiber lose, fiber coupling inefficiency, fiber concentration and response to noise, either random or periodic, produced by a variety of internal and external sources.

In current medical applications, it is desirable that the fiber distribution system be relatively small, flexible, and highly efficient. The size requirement becomes more crucial as in situ blood gas monitoring techniques are being developed. For example, a blood gas catheter or sensor may be inserted into and left in a patient's body for a long period of time to provide continuous monitoring of specific conditions. The catheter tip includes the analyte-sensitive indicator molecule. For the patient's comfort, the catheter tip should be as small as possible. To accommodate this desirable size characteristic, a single fiber extending to the catheter tip is desirable. The remainder of the distribution system is then sized in proportion to the catheter tip fiber for maximum efficiency.

In a single-fiber sensor system, a single optical fiber carries the measuring signal to the indicator molecule, as well as carries the reflected or emitted indicator signal from the indicator molecule. One useful characteristic of a single-fiber system is that it is reducible to nearly one-half the size of the duofiber system at the sensor tip. However, a single-fiber sensor presents problems related to the small amount of light a single fiber, as well as the related distribution system, can carry, and the ability of the system to distinguish indicator signals from measuring signals that are reflected back at imperfect fiber connections. The former problem is especially prevalent in analog-based sensors, the intensity of the signal produced at the sensor rather than the mere existence of the signal, as in a digital system, is significant. Each change in signal intensity that is not traceable to a constant in the distribution system will be attributed to a parameter in the monitoring process. Thus, the optical fiber distribution system must be highly predictable and reliable in order to provide useful monitoring results.

One known distribution system for a single-fiber sensor system includes lengths of optical fiber, a dividing connector, a mixing section, a transmitting connector and a tip connector. The optical fiber lengths are of first and second diameters, the second diameter being larger than the first diameter and being substantially equal to the diameter of the sensor tip fiber. The dividing connector connects at least three intermediate fibers of the first diameter to the signal-generating component to thereby receive intermediate signals. The mixing connector connects a mixing fiber of the second diameter to the intermediate fibers to thereby receive the intermediate signals and blends them into a single mixed signal. The transmitting connector connects a transmitting fiber of the first diameter to the mixing fiber to thereby receive a portion of the mixed signal. The tip connector connects the transmitting fiber to the sensor tip fiber to thereby transmit the mixed signal to the sensor tip, and connects an indicator fiber of the first diameter to the sensor tip to thereby transmit a portion of the resulting indicator signal returned from the sensor tip to the signal-measuring component.

However, the use of fibers of different sizes in the distribution and a multiplicity of components in the distribution system can lead to inefficiencies in that system. The use of fibers of different diameters can result in lose of signal at the fiber interface. The multiplicity of connectors in the system can also result in a loss of transmitted signal. A multiplicity of parts in the distribution system of the prior art also leads to complexities in manufacture which would result in a distribution system of reduced efficiency as well as a system having substantial complexity in its manufacturing process.

SUMMARY OF THE INVENTION

However, it would be desirable to eliminate certain components, use optical fibers of a single diameter and devise a modular configuration which would incorporate a combination of light emitting diodes (LED's), photodiodes and optical couplers to provide a smaller, simpler distribution system. It would further be desirable if the proposed system could incorporate a method of reducing the reflected light at the photodiode interface. Further, it would be desirable if the proposed distribution system could incorporate an improved temperature stabilization method for the LEDs associated with the system, such stabilizing method to improve the stability of the output of the LEDs, thereby minimizing the effect of ambient temperature on LED output.

Accordingly, the proposed distribution system of the present invention incorporates a sensor that utilizes an analyte sensitive indicator molecule to monitor the concentration of the analyte, the sensor having a signal generating component for producing first and second optical signals of distinct wavelengths, in which the first signal wavelength is such that the optical intensity is altered by the indicator molecule in proportion to the presence of the analyte, and the second signal wavelength normalizes optical path losses. The system includes a single fiber sensor tip that includes the indicator molecule and a signal measuring component for receiving signals from the distribution system.

The system further comprises lengths of optical fiber of a single diameter, with a first optical coupler combining a first signal corresponding to the wavelength of the first signal and the wavelength of a second signal, a second optical coupler transferring the combined or mixed signal from an interface defined by the first and second optical couplers to the sensor tip and to a first photo reference device and directing the signal returned from the sensor tip to a second photo-signal measuring device and connecting an indicator fiber to the sensor tip to thereby transmit a portion of the resulting indicator signal return from the sensor tip to the photo-signal measuring device.

Because the light emitting diode, like all light sources, changes wavelength and output power with temperature, the improved distribution system of the present invention incorporates therein a temperature control mechanism for the LED.

Additionally, because the signal and reference photodiodes of the improved system face each other through the optical coupler, any light reflected from the reference photodiode surface will corrupt the sensor signal being measured. Accordingly, the improved system incorporates an improved photo diode assembly designed specifically to reduce internal reflection. In addition to incorporating the improved features noted above, the modular distribution system of the present invention increases delivered power from the optical source to the sensor. Further, the improved system increases the dynamic range of measurements. Additionally, the LED cooling system provides that there will be little or no wavelength change in the source with temperature changes in the ambient environment. An improved cooling system means lower temperature coefficient and increased efficiency of the system. Additionally there are no optical connectors within the module, i.e., all fiber connections between above described components are fiber fused interfaces, thereby reducing the size and increasing the efficiency of the distribution system.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a block diagram of a representative system for an absorbance based sensor, including an optical fiber distribution system in accordance with the invention;

FIG. 2 is a schematic diagram of the improved fiber optic distribution system of the present invention;

FIG. 3 is a schematic representation of the improved LED cooling system;

FIG. 4 is a exploded perspective view of the LED assembly;

FIG. 5 is an exploded perspective view of the photo diode assembly of the present invention; and FIG. 6 is a schematic drawing for a method of reducing internal reflection in the photo diode assembly of the present invention.

DESCRIPTION OF THE PREFERRED EMBODIMENTS

The optical fiber distribution system of the present invention is suitable for use in conjunction with a variety of physiological pH and blood gas concentration sensors. The distribution system is integratable into a single-fiber tip sensor system. Preferred embodiments of the distribution system will be described in conjunction with pH/pCO$_2$ absorption sensors. However, it is to be understood that the following descriptions are not meant to limit the present invention to use in conjunction with any specific sensor types.

FIG. 1 shows a representative sensor system 30 for determining the pH/PCO$_2$ concentration of gaseous compositions by measuring the absorbance change of various sensor indicator molecules by the composition. FIG. 1 is similar to FIG. 1 of U.S. Pat. No. 4,907,857 entitled "Optical Fiber Distribution System for an Optical Fiber Sensor" issued Mar. 13, 1990 and assigned to the assignee of the present invention ("the '857 Patent"). To the extent that an understanding of the optical fiber distribution system of the above noted patent is useful to an understanding of the present invention, the above noted U.S. patent is herein incorporated by reference. The system 30 includes: signal-generating component 32; optical distribution system 36; sensor tip 37; signal-measuring component 38; and microcomputer 40. The signal-measuring component 38 includes: signal and reference photodiodes or detectors 42a and 42b; signal and reference preamplifiers 44a and 44b; and signal converter 46.

The system 30 provides light excitation of a pH/$PCO_2$ sensitive composition 48, such as a phenol red based composition, sequestered in the sensor tip 37. The sensor tip 37 and composition 48 are submerged in an analyte-containing solution (not shown). The signals transmitted from signal-generating component 32, preferably a pair of differentially colored light emitting diodes (LEDs) 32a and 32b, pass through optical fiber distribution system 36. LED 32a generates a signal, termed measuring signal, that is of a wavelength that will be absorbed by the indicator molecule in composition 48 in proportion to the presence of pH/$PCO_2$ in the analyte-containing solution. LED 32b generates a signal, termed reference signal, that is of a wavelength that is geometrically reduced by the composition 48 so that the intensity of the signal reflected at the sensor tip is predictable. As the reference signal is transmitted through system 30, it is subject to known signal intensity reductions at the various component connections and at the sensor tip.

The distribution system divides the measuring and reference signals into intermediate signals and mixes those to produce a single mixed signal. The distribution system transmits a portion of the mixed signal to the reference photodiode 42b and a portion on to the sensor tip 37. At the sensor tip 37, the mixed signal encounters the analyte-sensitive composition.

The radiation in the mixed signal that corresponds in wavelength to the measuring signal is absorbed by the indicator molecule in proportion to the quantity of the analyte present in the analyte-containing solution. The radiation in the mixed signal that corresponds in wavelength to the reference signal is absorbed at a predictable rate by the analyte-sensitive composition. The unabsorbed or reflected signals are termed output or indicator signal. The distribution system transmits the indicator signal from the sensor tip to the signal photodiode 42a.

The signal and reference photodiodes 42a and 42b receive optical signals as input and output corresponding electrical signals. An example of a conventional signal detector is a p*material-intrinsic material-n*material (PIN) silicon component. The indicator signal is transmitted to indicator preamplifier 44a, and the mixed signal is transmitted to comparison-signal preamplifier 44b. The preamplifiers 44 transmit the amplified signals on to the signal converter 46, which converts the signals from analog to digital. The signals are then input into the microcomputer 40, which monitors the sensor's operation and acts as an input/output device for the system.

The microcomputer 40 analyzes the signals received from the signal-measuring component 38 to monitor the presence of the analyte as well as the distribution system operation. The measuring and reference signals in the mixed signal, and the reflected measuring and reference signals in the indicator signal are all distinguishable by their respective wavelengths at the signal-measuring component 38. Because the reference and measuring signals are generated at distinct time intervals, the signals can be isolated by time differentiation or multiplexing. The microcomputer 40 compares the intensity of the measuring signal received at the comparison component to that received at the indicator component to determine the quantity of the analyte in the solution being monitored. The microcomputer 40 also compares the intensity of the reference signal received at the comparison component to that received at the indicator component to determine whether the distribution system is operating accurately.

While there are certain similarities to FIG. 2 of the '857 Patent and FIG. 2 of the present invention and the optical distribution system of both figures achieves a similar end result, the means by which such end result is accomplished are substantially different. For example, couplers C1 and C2 ($2 \times 2$ HCS optical couplers) generally replace the mixed-signal component, the indicator component and the comparison component of the '857 Patent. In the '857 patent, the mixed signal component couples measuring and reference signals to produce a mixed signal, transmits the mixed-signal to the sensor tip 37, and transmits an indicator signal back from the sensor tip to the distribution system. The indicator component transmits the indicator signal from the mixed-signal component to the indicator-signal detector of the signal-measuring component. The comparison component transmits a mixed signal from the mixed-signal component to the comparison-signal detector of the signal measuring component.

In the preferred embodiment of the present invention of FIG. 2, a single diameter of optical fiber is used. A suitable diameter for the fiber is 225 micrometers ($\mu$m) measured across the outer claddings. The fiber optic couplers C1 and C2 of the present invention ensure that a signal of predictable intensity is transmitted between adjacent fibers.

The optical coupler C1 receives measuring and reference signal inputs from the signal-generating component 32, which preferably includes a first measuring signal source 32a and a second reference signal source 32b.

Suitable signal sources for pH and $PCO_2$ sensors utilizing a phenol red based analyte-sensitive composition are a green light emitting diode (LED) 32a and a near-infrared LED 32b, for generating measuring and reference signals, respectively. Connected to the measuring LED 32a and the reference LED 32b are respective input fibers 58a and 58b. Fiber fusion spliced interfaces 59a and 59b are provided between high numerical aperture (NA) glass optical fibers 58a and 58b and optical coupler C1 (a hard-clad-silica (HCS) optical coupler). Fiber-fused interfaces between the optical components of the distribution system increase the efficiency of such components and reduce the overall size of the system. LED assembly 32 is described in greater detail below.

Optical coupler C1 combines the light from the measuring signal source LED 32a and the reference signal source LED 32b for transmission into a single optical fiber 61. An absorber 62 absorbs all incoming light and prevents output of reflected light. Fiber fusion spliced interface 61a is interposed between optical fiber 61 and a second optical coupler C2. The output end of interface 61a of the coupler C1 transfers the combined signal to a second optical coupler C2 (also a HCS 2×2 optical coupler) which transmits the light of the combined signal from the two signal sources 32a and 32b to the sensor interface and to the system reference photo diode 42b through fiber fusion spliced interface 61b and optical fiber 82. The optical coupler C2 also transmits the returned light from the sensor 37 to the signal photo diode 42a through optical fiber 69 and fiber fusion spliced interfaces 69a and 69b.

LED assembly 32 is shown in greater detail in FIGS. 3 and 4. The LED 32, like all light sources, changes wavelength and output power with temperature. The efficiency of the sensor changes with wavelength. In order to insure proper sensor operation, the temperature of the LED 32 must be controlled. The LED assembly 32 comprises a mounting block or thermal block 70 having supported therein the optical fiber 58. The fiber is received in a positioning tube 71 mounted in a groove 72 provided in the mounting block 70. While it is desirable to use a single positioning tube 71 to receive and hold the optical fiber 58, it is also possible to receive and hold optical fiber 58 with a series of concentric tubes similarly positioned as the tube 71 in FIGS. 3 and 4. The LED assembly 73 is shown mounted in a cavity 74 of the mounting block 70 with the LED assembly comprising a thermal cooler 76, an LED chip 77 and an LED lens 78.

To accomplish temperature control and insure proper sensor operation, and a thermal electric cooler (TEC) 76 maintains the temperature of the LED near 20 degrees centigrade. In an alternative embodiment, it might be desirable to include an integrated thermistor in the LED assembly 32 for temperature sensing and to improve thermal stability. While fiber optic systems for telecommunications and aerospace applications use light sources in the infrared range of the spectrum (800 nanometers to 1300 nanometers), typically with power outputs in the milliwatt range, the sensor of the present invention requires a visible light LED. Since visible light LEDs are not optimized in terms of power output for fiber optic use, the lens 78 can be added to the LED package to increase the coupling efficiency of the emitted light into the fiber 58. While conventional optics theory would predict higher efficiency for an optical cooling mechanism which incorporates a lens, actual implementation did not meet theoretical predictions, and the preferred cooling mechanism of the present invention omits the lens 78.

As better seen in FIG. 4, the pigtailed LED assembly is mounted in the aluminum mounting block 70 for both conducting heat away and for removing ambient light. In the preferred embodiment, the optical fiber 58 is mounted within a metal sleeve 71 to align the optical fiber 58 in the groove 72 of the metal block 70. Brass alignment tube 71 receives the optical fiber 58. The tube 71 is then glued into the groove 72 in the mounting block 70.

A cap 79, which serves as a dust cover and blocks ambient light, is mounted on top of the mounting block 70. An indicator button or marker element 80, which is colored either red or green to indicate either a signal LED assembly 32a or a reference LED assembly 32b, is mounted on top of the metal cap 79. The LED assembly 73 is mounted to the back of the block 70 by screws 81.

The optical fiber 58 is mounted within the metal sleeve 71 and positioned in front of the LED chip 77 to provide an air gap therebetween to obtain maximum coupling efficiency while minimizing mechanical motion effects. Although the lens 78 is omitted in the preferred embodiment, an air gap is provided between the LED chip surface and the fiber end to reduce any effects due to temperature variations between the two components.

A typical signal wavelength for the LED signal assembly 32a is 565 nanometers (nm). For the reference LED assembly 32b the reference wavelength is in the near infrared range, e.g., 815 nm. The typical optical fiber for the LED pigtail has a core diameter of 200 micrometers (μm). The cladding diameter is about 225 μm, the buffer diameter is about 500 μm, the fiber construction is hard clad silica (HCS) and the numerical aperture is 0.48.

As seen in FIG. 2, the signal photo diode 42a and the reference photo diode 42b face each other through the optical coupler C2. However, any light reflected from the surface of the reference photo diode 42a will corrupt the sensor signal being measured.

The method and apparatus used to solve this problem is shown in FIGS. 5 and 6. The optical fiber 82 which illuminates the reference photodiode 42b is placed at a specific height and angle over the surface. The open area between the optical fiber 82 and the photo diode surface is filled with an appropriate index of refraction material. Since the optical fiber 82 is tilting away from the surface of the photo diode 42b, the apparent fiber diameter is reduced. The percent of refracted light which enters back into the fiber is determined as follows:

$$\frac{\text{(Apparent Fiber Surface Area} - \pi(D_1/2)^2)}{\text{(Reflected Light Surface Area at Height Fiber is placed above photo diode surface} - \pi(D_2/2)^2)}$$

This method reduces the level of reflected light reentering the system to 0.1% (i.e., −30 db) or less. As shown in FIG. 5, the pigtailed photodiode assembly 90 comprises a mounting block 92 to which the signal photodiode 42a is attached in a rear portion thereof. The reference photodiode 42b is attached to the block 92 adjacent to and generally parallel with the signal photodiode 42a.

The fiber-mounted-in-a-tube configuration for the photodiode assembly 90 is comparable to the fiber mounting configuration for the LED assembly 32. Optical fiber 69 of optical coupler C2 is received into alignment tube 93 and thereafter inserted into the mounting block 92 at opening 94. Optical fiber 82 of the coupler C2 is mounted in the companion alignment tube 95 which is mounted in the groove 96 which in provided at an angle roughly 45 degrees from the angle at which the fiber 69 intersects the block 92, with opening 97 therein corresponding generally to the configuration schematically shown in FIG. 6.

The configuration of the photodiode assembly of FIG. 5 reduces the internal reflection caused by the reference photodiode 42b to a value such that the reflected intensity returning to the signal photodiode 42a is small compared to the coupler directivity. In the mounting of the reference photodiode 42b and the signal photodiode 42a shown in FIG. 5 the holding block has been machined to accept the metal sleeve surrounding the fiber, each fiber at the optimal angles for the reference photodiode and the signal photodiode.

Typical photodiode specifications provide for responsivity for both the signal and reference photodiodes to be typically about 0.300 A/W. Back reflection of the reference photodiode is limited to −30 decibels (db). The optical fiber has a typical core diameter of 200 μm, a cladding diameter of 225 μm, a buffer diameter of 500 μm, with a fiber composition of hard clad silica (HCS) and a numerical aperture of 0.48.

In operation, the optical coupler C1 mixes the measuring and reference signals into a single mixed signal. The second optical coupler C2 has two functions; it transmits the light from the sensor interface into the system reference photodiode 42b and directs the returned light from the sensor 37 to the signal photodiode 42a.

The two optical sources 32a and 32b are time multiplexed to remove ambient light effects and motion artifacts.

Signals from the two detectors 42a and 42b for both wavelengths, the signal wavelength and the reference wavelengths, are demodulated, and then compared using a standard radiometric algorithm in order to determine the change of state for the sensor.

The ratio is as follows:

$$\text{RATIO} = \frac{PD\text{-}S\,(G) \times PD\text{-}R\,(N)}{PD\text{-}S\,(N) \times PD\text{-}R\,(G)}$$

The PD-R or the reference photodiode 42b monitors changes in light source intensity for both the reference (LED N) and signal (LED G) sources 32a and 32b, whereas PD-S or the signal photodiode 42a monitors the relative variation between the LED-G and LED-N signals returning from the sensor. In operation, the coupler C1 mixes the measuring and reference signals into a single mixed signal. The coupler C2 connects transmitting fiber 69 to tip fiber 66. The opposite end of the tip fiber 66 is connectable to the sensor tip 37 or to other fibers immediately positioned relative to the tip. Tip fiber 66 is connected to any number of sensor tips by connecting devices such as the fiber fusion splices 69a and 69b shown in FIG. 2. Since the characteristics of the sensor tip, i.e., the analyte-sensitive composition in the tip, define the analyte to be monitored, the distribution system can be used for a variety of sensor applications.

During operation, a portion of signals travelling away from the sensor tip through the tip fiber 66 are passed to the optical coupler C2. As is the case with most fiber connections, a portion of the mixed signal passing through optical coupler C2 towards the sensor tip is reflected back into the transmitting and indicator branches of the coupler C2 due to characteristics such as changes in the index of refraction across the connecting space. These reflected signals are transmitted through optical coupler C2 into the signal photodiode 42a.

Since the reflected signals are the same wavelength as the indicator signals, they must be differentiated from the indicator signals, otherwise the intensity of the indicator signals will be increased by the addition of the reflected signals. The photodiode assembly 90 of FIG. 5 reduces the effects of such reflection at the reference photodiode 42b. Reflected indicator signal differentiation is also done by controlling the monitoring process, i.e., controlling the quantity of the signal passed through the system. This control is a function of the microcomputer 40.

Sensor tip 37 is directly connected to the signal photodiode 42a through the coupler C2. A portion of the mixed signal is routed from the first optical coupler C1 through the second optical coupler C2. In one preferred mode of operation, measuring signal is generated at signal generator 32a at specific time intervals to provide analyte concentration readings. The readings for pH and $PCO_2$ are obtained by comparing the intensity of the measuring signal wavelength band of the mixed signal with the intensity of the measuring signal wavelength band of the indicator signal.

A reference signal is generated at signal generator 32b at specific time intervals in order to perform checks on the distribution system operation. Because the near infrared light is a reference wavelength for sensors used in a phenol red based composition, the change of intensity of the reference signal as it is transmitted from the signal-generating component to the signal-measuring component is predictable, based on the known reductions at the fiber interfaces and at the sensor tip. If the intensity of the reference signal received at the indicator component is not as expected when compared to the intensity of the reference signal received at the comparison component, it is an indication that a malfunction,, i.e., fiber break or misconnection has occurred within the distribution system. This further indicates that the measuring signals indicative of analyte concentration may be subject to the same malfunction.

The optical fibers used in the described embodiments of the optical fiber distribution system are preferably hard clad silica. Other types of optical fibers, such as plastic or glass, are also suitable for the present invention. The use of a single fiber of a single diameter throughout the distribution system of the present invention avoids the signal loss experienced when the end of a smaller diameter fiber is completely subtended by the end of a larger diameter fiber. Such signal loss is experienced as the signal travels from the larger diameter fiber to the smaller diameter fiber. Further, the use of fiber fused interfaces at fiber/coupler interfaces increases system efficiency by minimizing optical losses at such interfaces and reducing the overall size and complexity of the distribution system of the present invention. A specific thermal control assembly improves the stability of the signal output of the sensor, and a specific configuration for the photodiode assembly substantially reduces internal reflection caused by the fiber interface for the reference photodiode of such assembly.

While preferred embodiments of the present invention have been illustrated and described, it will be appreciated that the various changes can be made therein without departing from the spirit and scope of the invention. The appended claims more appropriately describe the breadth of the invention.

The embodiments of the invention in which an exclusive property or privilege is claimed are defined as follows:

1. A distribution system for a sensor that utilizes an analyte-sensor indicator molecule to monitor the concentration of an analyte, the sensor having:
    a signal-generating component for producing first and second optical signals of distinct wavelengths, the first signal wavelength being such that the signal intensity is altered by the indicator molecule in proportion to the presence of the analyte, the second signal wavelength normalizing optical path losses, a single-fiber sensor tip that includes the indicator molecule; and a signal-measuring component for receiving signals from the distribution system, the distribution system comprising:

lengths of optical fiber of a single diameter, a first optical coupler combining a first signal corresponding to the wavelength of the first signal and the wavelength of the second signal; and a second optical coupler transferring the combined signal from an interface defined by said first and second optical couplers to the sensor and to a first photo-reference device and directing the signal returned from the sensor to a second photo-signal measuring device; whereby the intensity of said first signal is maximized at the first optical coupler, the intensity of said first signal being bounded by the transmission of the second signal of adequate intensity such that the intensity of the indicator signal of a wavelength corresponding to the wavelength of the second signal received by the signal-measuring device is suitable for monitoring the operation of the distribution system.

2. A distribution system as claimed in claim 1 wherein the signal generating component comprises an LED assembly for generating first and second optical signals of distinct wavelengths, the LED assembly comprising a mounting block, fiber support and alignment means for aligning the optical fiber with the LED assembly, retention means for retaining the fiber support means within the mounting block; the fiber retention means retaining the fiber in a position displaced from the LED assembly, such displacement operative to stabilize the signal output of the LED assembly.

3. A distribution system as claimed in claim 2 wherein a lens element is disposed between the LED assembly and the fiber end to further stabilize signal output of the LED assembly along the optical fiber of the system.

4. A distribution system as claimed in claim 2 wherein the LED assembly incorporates a thermal electric cooler to control the thermal stability of the LED.

5. A distribution system as claimed in claim 4 wherein an integrated thermistor is included in the LED assembly for temperature sensing and to improve thermal stability.

6. A distribution system as claimed in claim 1 including a photodiode assembly having a signal photodiode and a reference photodiode, wherein a respective signal reference optical fiber and a respective signal optical fiber are connected to the assembly, and one end of the signal reference optical fiber is mounted in the photodiode assembly at a specific height and angle above the surface of the reference photodiode, the open area between the reference optical fiber and the reference photodiode surface is filled with appropriate index of refraction material to reduce internal reflection of the reference photodiode within the photodiode assembly.

7. A distribution system as claimed in claim 6 wherein the percentage of refracted light which enters back into the reference optical fiber is determined as follows:

$$\frac{\text{(Apparent Fiber Surface Area} - \pi(D_1/2)^2)}{\text{(Reflected Light Surface Area at Height Fiber is placed above photo diode surface} - \pi(D_2/2)^2)}$$

8. A method for monitoring the concentration of an analyte in a distribution system for a sensor that utilizes an analyte-sensor indicator molecule, the method including the steps of:

producing first and second optical signals of distinct wavelengths, the first signal wavelength being such that the signal intensity is altered by the indicator molecule in proportion to the presence of the analyte, the second signal wavelength normalizing optical path losses, providing a single-fiber sensor tip that includes the indicator molecule; and receiving signals from the distribution system, the method further including the steps of:

combining a first signal corresponding to the wavelength of the first signal and the wavelength of the second signal with a first optical coupler;

transferring the combined signal from an interface defined by a first and a second optical coupler to the sensor and to a first photo-reference device with a second optical coupler;

directing the signal returned from the sensor to a second photo-signal measuring device;

maximizing the intensity of said first signal at the first optical coupler; and bounding the intensity of said first signal by the transmission of the second signal of adequate intensity such that the intensity of the indicator signal of a wavelength corresponding to the wavelength of the second signal received by the signal-measuring device is suitable for monitoring the operation of the distribution system.

* * * * *